United States Patent [19]

Buchanan, Jr. et al.

[11] Patent Number: 4,514,362
[45] Date of Patent: Apr. 30, 1985

[54] BREATH SPECIMEN MIXER

[76] Inventors: Frank L. Buchanan, Jr., 4812 Frieda Dr., Los Angeles, Calif. 90065; Bob B. Buchanan, 23721 Monument Canyon Dr., Diamond Bar, Calif. 91765

[21] Appl. No.: 437,351

[22] Filed: Oct. 28, 1982

[51] Int. Cl.³ .......................... G01N 1/00; B01F 5/00; B01L 11/00
[52] U.S. Cl. .................... 422/99; 73/863.43; 366/338; 436/174
[58] Field of Search ........................ 422/50, 83, 84, 99; 366/336, 338; 138/42; 73/863.41, 863.43, 864.91; 220/437, 439, 448; 248/146

[56] References Cited

U.S. PATENT DOCUMENTS 4,136,976  1/1979  Leffelman .......................... 366/336
4,402,909  9/1983  Solazzi .............................. 422/50

FOREIGN PATENT DOCUMENTS 584660  10/1959  Canada ............................... 220/448
45-40634  12/1970  Japan ................................ 366/338

Primary Examiner—Barry S. Richman
Assistant Examiner—Joseph P. Carrier
Attorney, Agent, or Firm—Gausewitz, Carr, Rothenberg & Edwards

[57] ABSTRACT

A mixing chamber designed for ready disassembly is described in which a generally spherical-shaped outer container encloses an inner sphere. Entry and exit openings are provided on opposite sides of the outer sphere, so that breath specimens pass through the chamber between the outer surface of the inner sphere and the inner surface of the outer sphere and undergo thorough mixing with low back pressure over a wide flow range. The interior volume can be increased by using a hollow inner sphere with an opening through the wall thereof to permit the inner sphere to fill with breath specimen also.

2 Claims, 4 Drawing Figures

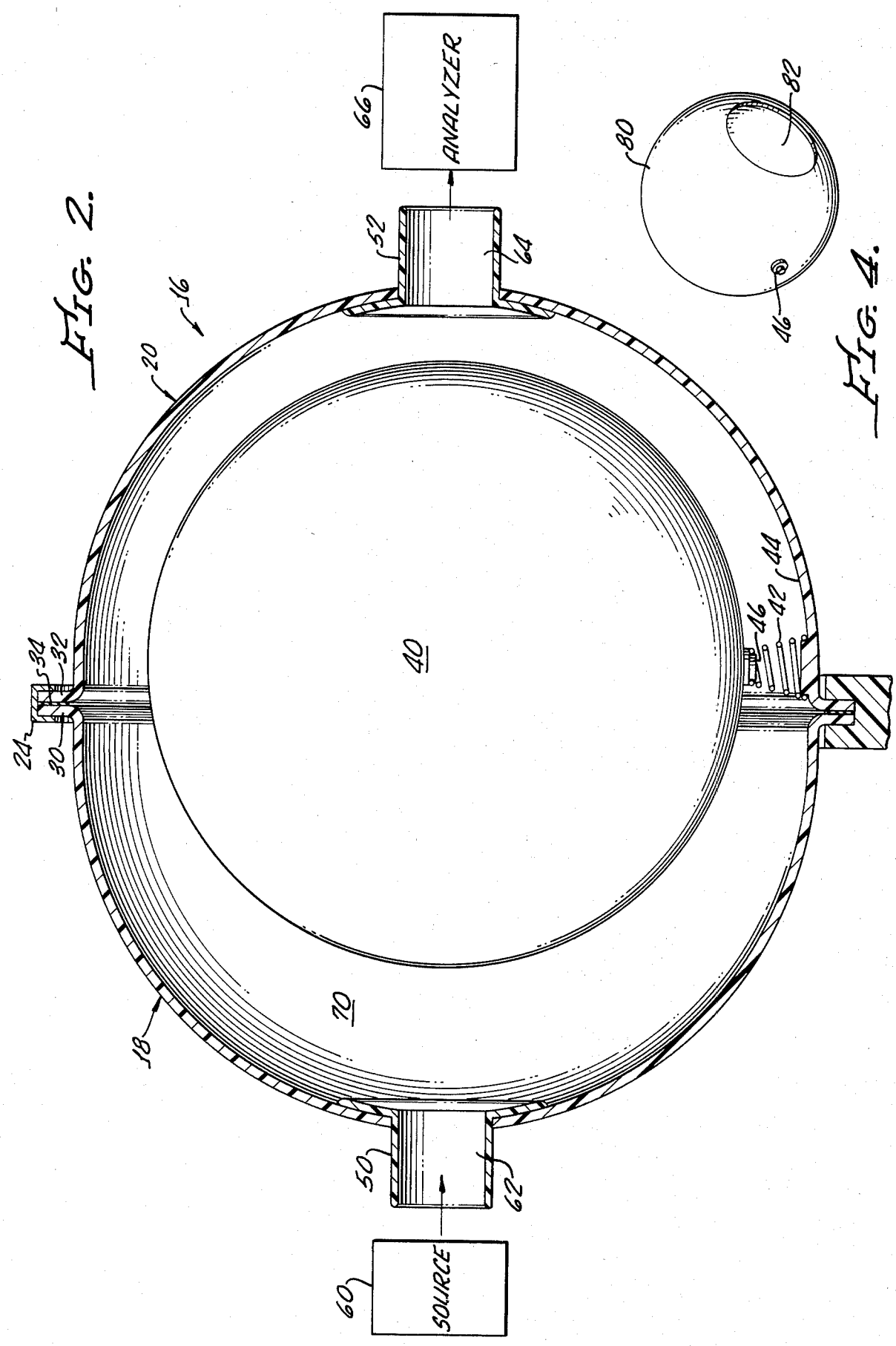

BREATH SPECIMEN MIXER

BACKGROUND OF THE INVENTION

This invention relates to techniques and devices for mixing heterogeneous gas specimens to obtain homogeneous blends. More specifically, it relates to methods and means for mixing breath specimens for medical analysis, which specimens are introduced into the devices of the invention directly by exhalation from the individual being tested.

The use of mixing chambers for obtaining breath specimens of patients for medical analysis is know. For example, in analyzing or treating respiratory ailments, or simply for performing diagnostic or metabolism tests, it is often desirable to obtain a full breath sample from a patient and to analyze the sample for, e.g., carbon dioxide content. Ideally, the analytical device is connected directly to a breath receiving apparatus, so that as the patient exhales, his breath specimen passes into the analytical device for immediate monitoring and analysis. However, the composition of an individual's breath is nonuniform, in that the initial exhalation delivers a gaseous composition containing an amount of carbon dioxide which differs from that contained at the end of an exhalation. This results in variable results in the analytical determinations, depending upon just what portion of a particular exhaled volume of breath is sampled by the analytical equipment.

It has been contemplated to take an entire exhalation volume of breath and thoroughly mix it before analyzing it or sampling it for analysis. Typically, patients exhaled into a collapsible bag, and then after the breath specimen was maintained in the bag long enough to ensure thorough mixing, a sample of the contents was removed and analyzed. Other devices have used large baffled boxes in which mixing was attempted by forcing a breath specimen to pass through the box and around a system of baffles designed to enhance the mixing of all the breath constituents. Still other devices relied upon using a motor and fan to thoroughly mix a breath specimen before analysis.

Each of the prior art techniques suffered from one or more deficiencies. Some produced a high back pressure, so that when the patient attempted to exhale into the mixing device, the pressure built up, especially at high flow rates, making it difficult, uncomfortable, or inefficient for the patient to exhale to the maximum extent. This problem was aggravated in the case of individuals having respiratory ailments or in the case of small children with inadequate capacity to exhale against high back pressures.

Other prior art devices were slow to use or resulted in uncertainties as to their mixing efficiency, so that it was not feasible to use them in a continuous manner such that a patient could exhale repeatedly directly through the mixing device into the analytical equipment.

Prior art devices have also been generally difficult to clean, so that contamination between consecutive users was a risk. Also, some devices of the prior art were devised for use with an average size of breath specimen and were not amenable to ready adjustment for differences in the size of breath specimen between small children and adults.

The problems and deficiencies of the prior art can be overcome or greatly alleviated in accordance with the present invention

SUMMARY OF THE INVENTION

This invention contemplates a mixing chamber for breath specimens which is highly efficient and produces a low back pressure. The chamber may provide also for quick disassembly for cleaning or for modification to vary the useful volume relative to the dead space in the chamber.

The chamber includes a globe suspended within a hollow shell, the globe being smaller than the interior of the shell, so that a space exists substantially entirely around the globe between the globe and the shell for passage and mixing of the breath specimen. In its particularly preferred embodiments, both the shell and the globe are generally spherical in shape, the shell being provided with inlet and outlet openings on opposite sides of the shell.

The mixing chamber may be adapted for providing a variable dead space by employing a hollow globe having an opening therein so that a breath specimen can occupy the space in the interior of the globe, as well as the space between the globe and the inner wall of the shell. The opening in the globe should be sufficiently large as to ensure rapid and thorough ingress and egress of the breath specimen, yet not so large as to greatly affect the overall configuration of the globe. Typically, the diameter of the opening in the side of the globe is contemplated to range from a size of about one half to about one and a half times the radius of the globe. In any event, the opening should not be so large as to approach the diameter of the globe, i.e., to convert the globe into a hemisphere.

A user, e.g., a respiratory patient or person undergoing diagnostic testing, uses the mixing chamber by exhaling into the opening on one side of the shell. The breath specimen passes about the outer surface of the globe and undergoes vortexing, which produces highly efficient mixing, before the specimen reaches the outlet on the opposite side of the shell. The thoroughly mixed breath specimen can then be passed directly to analytical equipment for analysis therein.

The optimum relationship between the size of the globe and the inside diameter of the shell depends upon the precise shape of the shell and globe and the amount of back pressure and flow rate of specimen for which the mixing chamber is designed. Typically, however, outstanding results can be achieved when the volume occupied by the globe makes up between about one third and two thirds of the volume of the shell. While larger globes can be used, excessive back pressures may be encountered, especially at high breath specimen flow rates. Conversely, if smaller globes are used, incomplete mixing may result, so that samples taken from th exit opening of the shell may not be truly representative of the overall specimen composition.

BRIEF DESCRIPTION OF THE DRAWINGS

FIG. 2 is a cross section taken along lines 2—2 of FIG. 1, also indicating schematically the source of the breath specimen and the analyzer used on the mixed product;

FIG. 4 shows an alternative embodiment of the globe of FIG. 2.

DETAILED DESCRIPTION OF THE INVENTION

Figure 1:
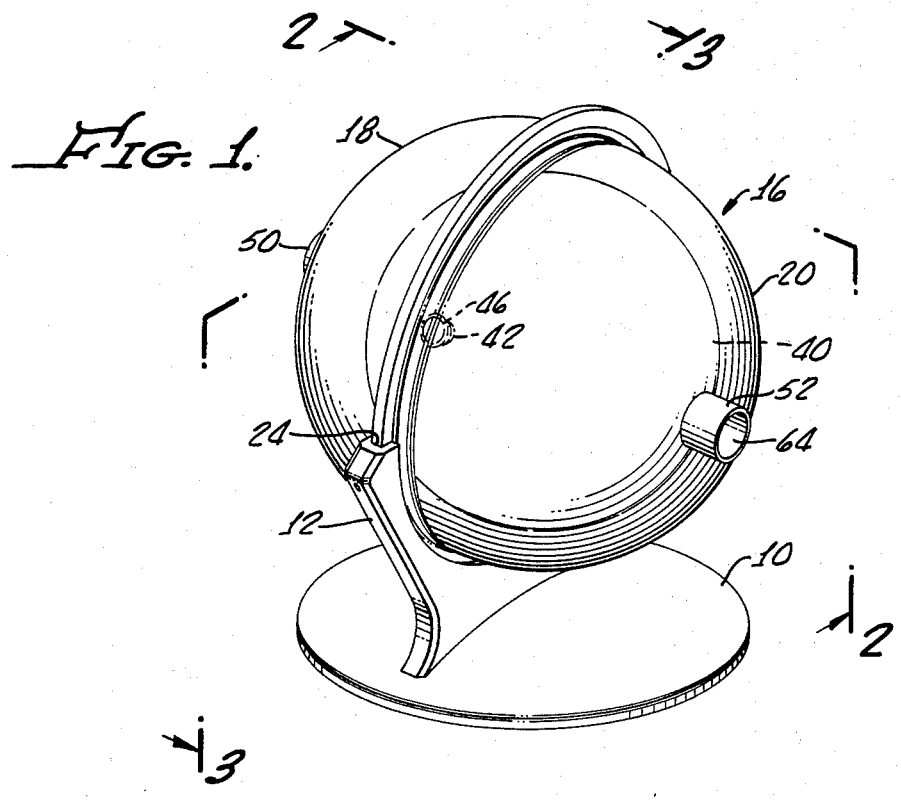
FIG. 1 is a perspective of a mixing chamber constructed in accordance with the invention.
Figure 3:
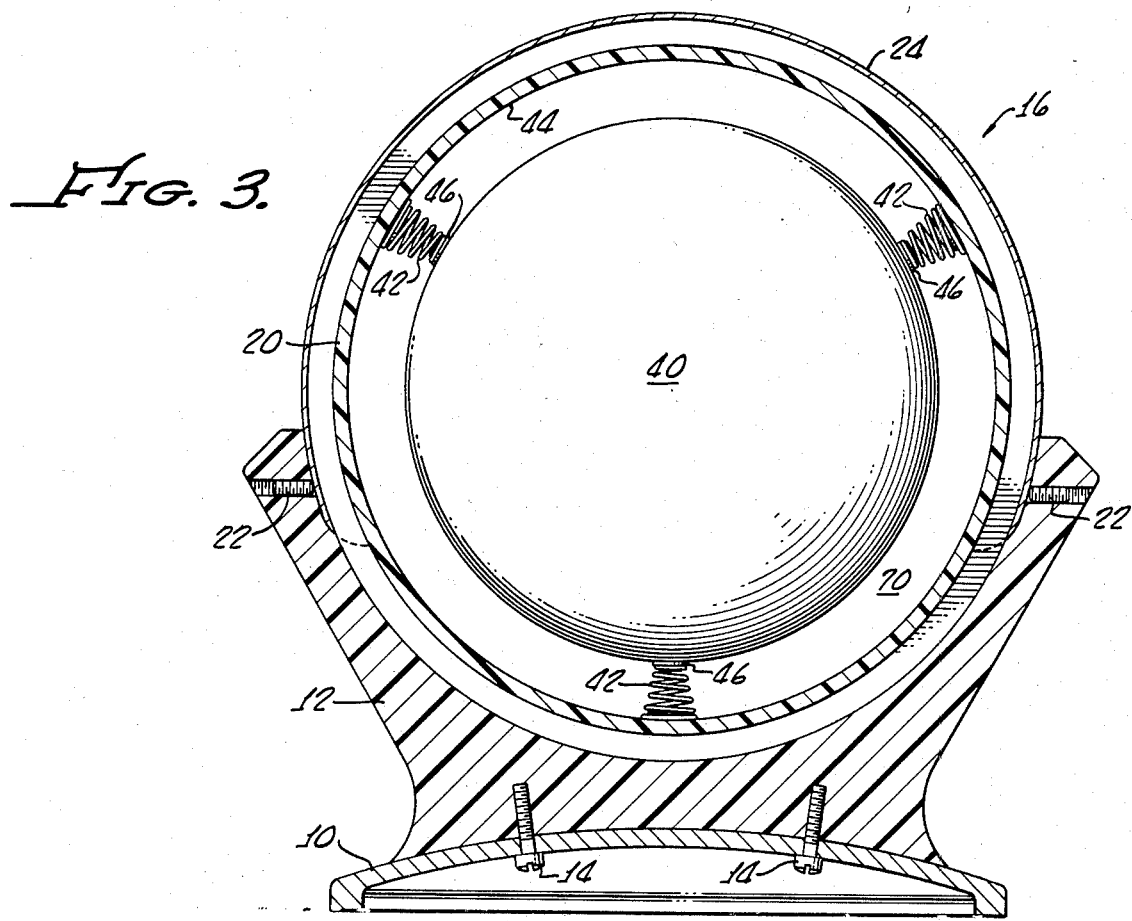
FIG. 3 is a cross section taken along lines 3—3 of FIG. 1.

As shown in FIGS. 1 and 3, a base member 10, preferably of steel or other sturdy material, supports a vertical pedestal 12 and is connected thereto by fasteners 14. A mixing chamber 16 comprising a front half shell 18 and a rear half shell 20 (see FIG. 2), whose concave sides face one another, is secured by set screws 22 in channel 24 of the pedestal. Both the pedestal and the mixing chamber may be comprised of acrylic plastic, or other suitable material, for handling breath specimens. In a preferred embodiment of the invention, an acrylic plastic chamber approximately eleven inches in diameter is used.

The channel 24 of pedestal 12 grips flange members 30 and 32 of half shells 18 and 20 compressing them to form a fluid tight seal sandwiching gasket 34.

A globe 40 suitably sized to fit within mixing chamber 16 is removably mounted in mixing chamber 16 by springs 42 affixed about the inner wall 44 of rear half shell 20. In a preferred embodiment of the invention, excellent results are achieved using a substantially spherical globe approximately eight inches in diameter and formed of plastic, or other suitable material.

The glove is equipped with pins 46, which may be integrally formed with the globe or adhesively attached thereto, and are adapted to fit compatibly with springs 42 to suspend the globe within the mixing chamber. As shown in FIG. 2, the globe need not be centered within the mixing chamber 16, but may be positioned such that its center is slightly to the rear of the center of the mixing chamber.

An inlet port member 50 is provided in front half shell 18, and a substantially axially aligned outlet port member 52 is provided in rear half shell 20. These port members may be fabricated of any convenient material, such as plexiglass or other material, which can be readily secured to the half shells. In the preferred embodiment of the invention employing the aforementioned mixing chamber and globe, port members approximately 13/16 in inside diameter with walls 3/16 inch thick have been found to have sufficient structural characteristics to provide excellent results.

FIG. 2 also depicts a source 60 of a breath specimen (which may be a patient or other person whose breath is to be analyzed). The specimen is introduced through the opening 62, through inlet port member 50, and front half shell 18, and exits from the mixing chamber through opening 64, through outlet port member 52, and rear half shell 20, from which it passes to a breath specimen analyzer 66, after being thoroughly mixed in mixing chamber dead space 70. The dead space 70 surrounds all, or substantially all, of the globe 40 providing a relatively symmetrical cross section about the globe, as shown in FIG. 3.

For the particularly preferred design of the mixing device described above, the dead space 70 constitutes approximately 5.3 liters for a globe approximately eleven inches in diameter within a chamber of approximately eleven inches in diameter. Such device has been found to produce very low back pressures when in use, and tests at fixed flow rates have produced the following results:

| LITERS PER MINUTE | BACK PRESSURE mm H$_2$O |
| --- | --- |
| 0 | 0 |
| 100 | 0.48 |
| 200 | 1.6 |
| 300 | 3.5 |
| 400 | 5.9 |
| 500 | 8.3 |
| 600 | 12.6 |

While these data were obtained using a generally round shell, even better results with lower back pressures may be obtained using elongated configurations.

FIG. 4 shows an alternative globe 80, which may be used interchangeably with globe 40, to increase the residence time or volume of breath handled in a given specimen. The globe 80 is hollow and has an opening 82 which in an eight inch globe is preferably approximately three and a half inches in diameter. By using the open hollow globe, the capacity of the mixing chamber may be effectively approximately doubled to about ten liters for the above-described chamber. Thus, in using the invention herein, globes of various sizes may be used. In general, the units which have a smaller mixing chamber dead space 70 provide excellent mixing for high respiratory rates and moderate volumes. They offer extremely low back pressures and are excellent for pediatrics where small volume flows are expected. On the other hand, by using a globe of the same diameter but which is hollow and open as in FIG. 4, the mixing device provides excellent mixing for higher volume use, such as for analyzing breath specimens from individuals undergoing vigorous excerise, with only a slightly increased back pressure.

The mixing chamber of the invention thus provided for a variable dead space with excellent mixing over a very wide range of flow rates and extremely low back pressures. Also, a key and novel feature of the invention is that it is extremely easy to disassemble for cleaning or changing globes. Thus, to disassemble the mixing chamber, one merely loosens the set screws 22 and lifts the two half shells 18 and 20 out of the channel 24 of pedestal 12. The half shells are then separated, and their interior surfaces can be washed or sterilized, as desired, while the surfaces of the globe can also be cleansed. The same or different globe can then be pressed into position inside the spaced springs 42, which snap into position over the pins 46, thus, instantly suspending the globe within the mixing chamber. The two half shells are then reassembled about the gasket 34 and repositioned within channel 24 and secured in place by set screws 22. As far as is known, there is no other device capable of such rapid and simple disassembly for cleaning, inspection or change of mixing space volume.

The invention in its broadest embodiments comprehends a device in which a specimen is introduced into one side and forced to expand about a suspended mixing means and is then collected at the opposite side and withdrawn therefrom. While generally spherical or slightly oblong shells have been described, it will be appreciated that other variations are possible within the scope of alternative embodiments of the invention.

Many other uses and variations of the invention will be apparent to those skilled in the art, and while specific embodiments of this invention have been described, these are intended for illustrative purposes only. It is intended that the scope of the invention be limited only by the attached claims.

What is claimed is:

1. Apparatus for mixing a heterogeneous gas specimen to produce a substantially homogeneous product consisting essentially of:

a hollow container having means forming an inlet opening and an outlet opening coaxial with said inlet opening through the walls thereof for introducing said heterogeneous gas specimen and withdrawing said product, said container including an aligned pair of substantially hemispherically shaped halves and means for detachably clamping said halves together to form an easily disassemblable unit, the walls of said container defining a chamber which is substantially symmetrical about an axis centered in said openings, mixing means positioned within said container substantially spaced apart from the inner surfaces of the walls thereof for causing said gas specimen to be disbursed and mixed about said means upon passage through said container from said inlet opening to said outlet opening, said mixing means comprising a globe suspended within said container so that its center is positioned substantially on said axis of the inlet and outlet opening in said container, said globe ranging in volume from about one third to about two thirds the interior volume of said container, said globe being substantially concentric with said container but spaced apart therefrom, suspension means comprising a plurality of spring members affixed about the inner surface of one of said hemispherically shaped halves for detachably engaging said globe for suspending the same, while permitting said globe to be easily removed from said container, said globe including engaging means affixed to the outer surface of said globe and positioned to engage said spring means, said clamping means comprising opposing aligned flanges on said hemispherically shaped halves and an arcuate channel member for enclosing and sealingly clamping together the periphery of a substantial portion of said flanges, and a base member for supporting said container, said channel member being mounted on said base member facing arcuately upwardly, said channel member being sized to engage a substantial portion of but less than half of said periphery of said flanges.

2. Apparatus for mixing a heterogeneous gas specimen to produce a substantially homogeneous product consisting essentially of:

a hollow container having means forming an inlet opening and an outlet opening coaxial with said inlet opening through the walls thereof for introducing said heterogeneous gas specimen and withdrawing said product, said container including an aligned pair of substantially hemispherically shaped halves and means for detachably clamping said halves together to form an easily disassemblable unit, the walls of said container defining a chamber which is substantially symmetrical about an axis centered in said openings, mixing means positioned within said container substantially spaced apart from the inner surfaces of the walls thereof for causing said gas specimen to be disbursed and mixed about said means upon passage through said container from said inlet opening to said outlet opening, said mixing means comprising a globe supended within said container so that its center is positioned substantially on said axis of the inlet and outlet openings in said container, said globe ranging in volume from about one third to about two thirds the interior volume of said container, said globe being hollow and having an opening in its wall to permit said gas specimen to occupy both the space within said globe and the space between said globe and the walls of said container, the diameter of said opening ranging in size from about one half to about one and one half times the radius of said globe, said globe being substantially concentric with said container but spaced apart therefrom, suspension means comprising a plurality of spring members affixed about the inner surface of one of said hemispherically shaped halves for detachably engaging said globe for suspending the same, while permitting said globe to be easily removed from said container, said globe including engaging means affixed to the outer surface of said globe and positioned to engaage said spring means, said clamping means comprising opposing aligned flanges on said hemispherically shaped halves and an arcuate channel member for enclosing and sealingly clamping together the periphery of a substantial portion of said flanges, and a base member for supporting said container, said channel member being mounted on said base member facing arcuately upwardly, said channel member being sized to engage a substantial portion of but less than half of said periphery of said flanges.

* * * * *